United States Patent [19]

Larsen

[11] Patent Number: 5,362,321
[45] Date of Patent: Nov. 8, 1994

[54] CEMENT COMPOSITION AND METHODS FOR PRODUCING SAME

[75] Inventor: Søren B. Larsen, Aalborg, Denmark

[73] Assignee: Aalborg Portland A/S, Aalborg, Denmark

[21] Appl. No.: 938,046

[22] PCT Filed: Apr. 10, 1991

[86] PCT No.: PCT/DK91/00098

§ 371 Date: Nov. 12, 1992

§ 102(e) Date: Nov. 12, 1992

[87] PCT Pub. No.: WO91/15435

PCT Pub. Date: Oct. 17, 1991

[30] Foreign Application Priority Data

Nov. 4, 1990 [DK] Denmark .................. 936/90

[51] Int. Cl.$^5$ ............................................. C04B 22/08
[52] U.S. Cl. ................................. 106/713; 106/736; 106/766; 106/769
[58] Field of Search .............. 106/713, 736, 766, 769; C04B 22/08

[56] References Cited

U.S. PATENT DOCUMENTS

1,865,021 6/1932 Larmour.
4,572,739 2/1986 Rasmussen .................. 106/101
4,784,691 11/1988 Rasmussen .................. 106/89

FOREIGN PATENT DOCUMENTS

0224840 7/1985 Germany .................. 106/769

OTHER PUBLICATIONS

Chemical Abstract—"Change in the Electrode Potential of Zinc in Hardening Cement Paste" Berdov et al. (1989), vol. 12 pp. 52–55 (Russian).

Primary Examiner—Mark L. Bell
Assistant Examiner—Paul Marcantoni
Attorney, Agent, or Firm—Foley & Lardner

[57] ABSTRACT

A cement composition comprising 1) a cement containing water-soluble chromate and 2) at least one manganese(II) compound in an amount sufficient to reduce the amount of water-soluble chromate to at the most 2 mg of Cr(VI) per kg of the cement, the determination of the chromate content being carried out by elution of the composition in water for 15 minutes at a water/cement ratio 1, filtration and determination of the chromate content in the filtrate.

36 Claims, No Drawings

CEMENT COMPOSITION AND METHODS FOR PRODUCING SAME

FIELD OF THE INVENTION

The present invention relates to a cement composition with reduced content of water-soluble chromate, a method for reducing the amount of water-soluble chromate in a cement composition, and to methods for producing a cement composition with reduced content of water-soluble chromate.

BACKGROUND OF THE INVENTION

It is well known that water-soluble chromate in cement gives rise to allergic reactions in workers subjected to contact with cement-containing products. In particular, construction workers who are subjected to regular skin contact with wet cement such as wet cement paste, wet mortar, and concrete mixes, have a risk of contracting chromate-related eczema.

It is known to reduce the content of water-soluble chromate in a cement composition by addition of ferrous sulphate. The ferrous sulphate may be added, e.g., during the preparation of cement-containing mixes or during manufacture of the cement, vide e.g. WO 82/02040. The iron(II) sulfate reduces $Cr^{+6}$ to $Cr^{+3}$, the latter having low solubility in cement-water mixes. The reaction between $Fe^{+2}$ and $Cr^{+6}$ takes place in aqueous solution, e.g. when water is added to a cement containing iron(II) sulfate.

SUMMARY OF THE INVENTION

It has now been found that manganese(II) compounds are effective for reducing the content of water-soluble chromate in cement compositions. Manganese(II) compounds, even in technical grade, have the advantage that they can be easily milled or ground to a small particle size well suited for addition to cement or cement compositions to obtain a satisfactorily homogeneous distribution. Some manganese(II) compounds such as manganese(II) sulfate have the advantage that they are oxidation stable in dry cement compositions even at high temperature, are available as dry free-flowing powders in technical grades and have high chromate-reduction efficiency when they are interground with cement.

DETAILED DISCLOSURE OF THE INVENTION

Thus, in one aspect, the invention relates to a cement composition comprising 1) a cement containing water-soluble chromate and 2) at least one manganese(II) compound in an amount sufficient to reduce the amount of water-soluble chromate to at the most 2 mg of Cr(VI) per kg of the cement, the determination of the chromate content being carried out by elution of the composition in water for 15 minutes at a water/cement ratio of 1, filtration, and determination of the chromate content in the filtrate.

The cement is one which, if no measures are taken, contains water-soluble chromate in amounts which are objectionable from a health hazard point of view, typically amounts of above 2 mg of Cr(VI) per kilogram of the cement, determined as described above, this determination preferably being performed in accordance with Danish Standard DS 1020. In this standard method, an agent which forms a coloured complex with chromate, i.e. s-diphenyl carbazide, is added to the filtrate obtained following elution of the cement, whereupon the intensity of the coloured complex is measured spectrophotometrically, and converted into content of water-soluble chromate by means of a calibration curve. As will be understood, the content of water-soluble chromate in the filtrate may also be measured in other suitable manner.

It is normally preferred that the manganese(II) compound is present in the composition in an amount sufficient to reduce the amount of water-soluble chromate to at the most 1 mg, preferably at the most 0.5 mg, in particular at the most 0.1 mg, especially at the most 0.01 mg of Cr(VI) per kg of the cement component.

The amount of manganese(II) compound sufficient to obtain the above reduction in the content of water-soluble chromate will typically be an amount representing a molar excess, calculated on the chromate, and thus, the minimum amount of manganese(II) compound is dependent on the natural content of water-soluble chromate in the cement in question. However, as a guideline, the manganese(II) compound may be present in an amount corresponding to from 1 to 1000 mmol manganese(II) per kg of the cement component, in particular an amount corresponding to 5-100 mmol manganese(II) per kg of the cement, preferably 10-60 mmol per kg of the cement.

The manganese(II) compound may be a manganese(II) salt; a salt containing manganese(II), a partly oxidized manganese(II) salt; a product containing manganese(II) such as particles containing manganese(II) or a manganese(II)-containing amorphous phase, e.g. a glass phase.

As suitable examples of the manganese(II) compound may be mentioned a salt with a mineral acid or with an organic acid. The mineral acid salt may be the sulfate, hydrogen sulfate, chloride, bromide, carbonate, nitrate, nitrite, sulfite, sulfide, disulfide, dithionate, thiosulfate, thiocyanate, hydroxide, oxide, monohydrogen phosphate, dihydrogen phosphate, silicate or hydrates thereof, preferably the sulfate. It may also be a double salt such as ammonium manganese(II) sulfate or potassium manganese(II) sulfate. The organic acid salt may, e.g., be a carboxylic acid salt such as a salt with an alkanoic acid such as formic acid or acetic acid, or a salt with a hydrocarboxylic acid such as lactic acid, tartaric acid, citric acid, gluconic acid or malic acid or a salt with a sulfonic acid such as methylsulfonic acid, a naphtalene sulfonic acid or a melamine sulfonic acid. Another example of a manganese(II)-containing compound is manganese(II) oxide sulfate.

The manganese(II) compound may typically be manganese(II) sulfate such as a technical grade manganese(II) sulfate, preferably containing more than 20%, in particular more than 25%, especially more than 31% by weight of manganese, and it may be hydrated, such as monohydrated or partially monohydrated. Manganese(II) sulfate has several advantages, i.a. that it is available as a dry free-flowing powder even in technical grades, that technical grades are available as a fine powder, that it is oxidation stable even at high temperature, that it is cheap since it is available as a byproduct from the preparation of hydroquinone, and that it has high efficiency as a chromate-reducing agent for cement particularly when it is interground with cement. Furthermore, manganese(II) sulfate is not very hygroscopic and is available as $MnSO_4 \cdot H_2O$ in technical grades.

The manganese(II) compound may also be a manganese(II)-containing mineral, e.g. szmikite, rhodochrosite, manganosite, alabandite, punite, manganosiderite, oligonite, or manganolangbeinite.

A suitable manganese(II) compound may be a soluble manganese(II) salt, e.g. manganese(II) sulfate or manganese(II) acetate but the manganese(II) compound may also be of low solubility, e.g. manganese(II) carbonate. It is preferable that a manganese(II) compound with low solubility has a high specific surface area. This may for example be obtained by intergrinding the manganese(II) compound with the cement.

Manganese(II) sulfate is a soluble salt with a solubility of 985 g $MnSO_4.H_2O$ per liter of solution at 48° C. Even though manganese(II) sulfate is a soluble salt it has surprisingly been found that the efficiency can be increased by fine-grinding. Thus, in the cement composition of the invention, a reduced dosage of manganese(II) sulfate is required to reduce water soluble chromate when the manganese(II) sulfate is fine-ground.

Fine-grinding of the manganese(II) sulfate as well as other manganese(II) compounds may be done by intergrinding the manganese(II) compound with cement to a specific surface of the cement composition according to Blaine of more than 250 $m^2/kg$ preferably more than 300 $m^2/kg$ and most preferably more than 400 $m^2/kg$.

In a preferred embodiment, the manganese(II) compound is manganese(II) sulfate which is present in the cement composition in an amount of 0.01-10% by weight, in particular 0.1-1% by weight of cement.

It is especially interesting to note that suitable manganese(II) compounds may be ground or milled to a small particle size which may easily be distributed evenly in a dry composition, e.g. a mean particle size below 0.1 mm, preferably below 0.05 mm, in particular below 0.02 mm.

The cement may be any cement which contains a water-soluble chromate in an unacceptable amount. Common examples of such cements are Portland cements such as ordinary Portland cement, rapid hardening cement, and super rapid hardening cement; belite cement; low heat cement; blended cements; slag cements; Pozzolan cements; and the like, in particular Portland cements and blended cements.

In addition to the cement and the manganese(II) compound, the composition of the invention may further contain at least one material selected from aggregate material, reinforcing material, water, slaked lime, and cement and concrete additives.

The aggregate material may, e.g., be selected from fine aggregate such as sand, and coarse aggregate such as stone.

The cement or concrete additive may, e.g., be a retarding agent, a concrete plasticiser or superplasticiser, or an air entraining agent.

The composition of the invention may be in dry or wet form. A preferred composition is a composition in dry form wherein the manganese(II) compound is in the form of particles having a particle size as mentioned above.

The invention also relates to a method for reducing the amount of water-soluble chromate in a cement composition, said method comprising adding to the composition during the manufacture thereof a manganese(II) compound in an amount sufficient to effect a reduction in the content of water-soluble chromate to at the most 2 mg of Cr(VI) per kg of the cement, in particular at the most i mg, preferably at the most 0.5 mg, Cr(VI) per kg of the cement, the determination of the chromate content being carried out as mentioned above.

The addition of the manganese(II) compound may be carried out in a number of ways and at any of a number of stages of the preparation of the cement or the cement-containing composition.

Thus, the addition of the manganese(II) compound may, e.g., be carried out 1) by addition to cement clinker prior to or during grinding thereof;

2) by addition to semi-ground cement clinker;

3) by addition to a component added during the production of cement;

4) by addition of the compound as a concentrated aqueous solution to clinker in such a manner that the solution is evaporated;

5) by addition to cement powder prior to or during transfer thereof to a storage container or to a transport vehicle or prior to or during packaging thereof;

6) by addition to cement powder during transfer thereof from a transport vehicle to a storage container;

7) by addition to cement powder or a composition containing cement powder prior to mixing thereof with water;

8) by addition of the compound as a solution in cement mixing water; or 9) by addition of the compound in dry form or as an aqueous suspension or solution prior to, during or after the mixing of cement powder or a composition containing cement powder with water.

When the manganese(II) compound is added to cement clinker prior to or during grinding of the clinker or to semi-ground clinker, the addition may, e.g., be performed by means of a pneumatic transport system where the dosage of manganese(II) compound is controlled by means of a worm transporting device.

Addition of the manganese(II) compound to a component added during the production of cement may be by addition in admixture with e.g. gypsum, fly ash, slag, limestone, or similar components.

The addition of the manganese(II) compound as a concentrated solution to clinker in such a manner that the solution is evaporated may be performed by adding the solution to the clinker shortly after the rotary kiln while the clinker are still warm, or during the grinding of the clinker where the clinker are heated mechanically.

Addition of the manganese(II) compound to a cement or a cement composition during transfer thereof to a storage container or a transport vehicle, prior to packaging thereof, or during transfer thereof from a transport vehicle to a storage container may be performed by means of well-known techniques. Thus, the cement or cement composition may typically be transferred by means of a pneumatic transport system which incorporates a system for pneumatic addition of the manganese(II) compound in a well-known manner to the stream of cement or cement composition during the transfer thereof.

When adding the manganese(II) compound to cement or cement composition prior to the mixing thereof with water, the manganese(II) compound may be mixed in dry form with the cement or cement composition to give a homogeneous mixture. A particularly interesting example of this aspect is the addition of a manganese(II) compound during the manufacture of a dry mortar mix consisting of cement powder, sand, slaked lime and concrete additives.

When adding the manganese(II) compound as a solution in cement mixing water, the concentration of manganese(II) compound is adjusted according to the amount of manganese(II) compound and the amount of water required. Alternatively, the solution of manganese(II) compound may be more concentrated and constitute only part of the total amount of water required.

It may be summarised that when conducting the addition of a manganese(II) compound to a cement or cement composition at e.g. one of the above outlined steps, the manganese(II) compound may be supplied to the cement or cement composition as a wet powder; a solution; a concentrated solution; a dry, free-flowing powder; or mixed or interground with an inert powder to facilitate handling.

The invention is further illustrated by the following non-limiting examples.

EXAMPLE 1

Methods

Determinations of water-soluble chromate were carried out according to Danish Standard DS 1020 as described in detail below.

Measurements of the total reduction capacity of the cement mixes were also carried out. The reduction capacity is a measure of the excess reducing capacity present in the mixes, i.e. the ability to reduce added chromate. The reduction capacity was determined by extracting the cement mixes with solutions of potassium dichromate containing 50 and 100 mg of $Cr^{+6}$ pr. kg solution. The cement was extracted for 15 minutes at a water/cement ratio of 1. The reduction capacity was calculated by the following formula:

$$\text{Reduction capacity} = 50 - \frac{50 \times M50}{M100 - M50}$$

M50 = chromate content in filtrate after elution with a solution containing 50 mg of $Cr^{+6}$/kg.

M100 = Chromate content in filtrate after elution with a solution containing 100 mg of $Cr^{+6}$/kg.

Test method for water soluble chromate in cement according to Danish Standard DS 1020 (First Edition, July, 1984)

Method principle

The cement is eluted with water and filtered. To part of the filtrate, s-diphenyl carbazide is added which together with chromate in an acid medium forms a reddish-violet complex with an absorption maximum at 540 nm. The colour of the complex is measured photometrically and converted into content of water-soluble chromate by means of a calibration curve.

Reagents

All chemicals must be analytical grade. For the preparation of reagents and dilutions, chromate-free distilled or demineralized water is used.

Potassium permanganate, 0.02 M: 0.3 g of potassium permanganate ($KMnO_4$) is dissolved in 100 ml of water.

Sulphuric acid, 1.8 M: 96 ml of concentrated sulphuric acid ($H_2SO_4$, d=1.84 g/ml) are added to approx. 900 ml of water and diluted with water up to 1000 ml. Potassium permanganate, 0.02 M, is added until the colour is slightly pink.

Ethanol ($C_2H_5OH$, d=0.79 g/ml).

Indicator solution: 0.125 g of s-diphenyl carbazide [$(C_6H_5NHNH)_2CO$, 1,5-diphenyl carbohydrazide] is dissolved 25 ml of ethanol in a 50 ml volumetric flask. Water is added up to 50 ml. The indicator solution can be considered stable for up to 3 hours.

Chromate stock solution, 50 mg of $Cr^{+6}$ per litre: 0.1414 g of dried potassium dichromate ($K_2Cr_2O_7$) is dissolved in water in a 1000 ml volumetric flask and diluted with water up to 1000 ml.

Chromate standard solution, 5 mg of $Cr^{+6}$ per litre: 50.0 ml of chromate stock solution are measured into a 500 ml volumetric flask and diluted with water up to 500 ml. The standard solution must not be stored.

Apparatus

Magnetic stirrer with plastic-coated magnets or shaking apparatus.

Filter crucible with a capacity of about 60 ml and a porosity of 4.

Vacuum pump and suction flask for filter crucible or other equipment.

Spectrophotometer for measuring at a wavelength of 540 nm or a filter photometer with a filter providing maximum transmission around 540 nm.

Cuvette with a light path of 10 mm.

Measuring procedure

Calibration

Calibration solutions: 1.0, 2.0, 5.0, 10.0 and 15.0 ml of chromate standard solutions are transferred to 50 ml volumetric flasks. The calibration solutions contain 5.10, 25, 50 and 75 µg of $Cr^{+6}$, respectively. To each flask, 5 ml of sulphuric acid, 1.8 M, are added followed by dilution with water to a volume of about 40 ml. The solution is cooled to room temperature, 5 ml of indicator solution are added, and the flask is filled up to volume with water and shaken. The absorbance of the solution is measured with the reagent blind sample described below as the reference at a wavelength of 540 nm 15–30 minutes after the addition of the indicator solution.

Calibration curve: The calibration curve is drawn by plotting the measured absorbance values versus the content of $Cr^{+6}$. The calibration curve must be linear and should be checked regularly and always following exchange of reagents.

Analysis

The reagent blind sample is prepared as described above but using water instead of standard solution.

Elution: 25.0 g of cement are transferred to a 100 ml beaker and 25.0 ml of water added. The slurry is agitated vigorously with a magnetic stirrer or a shaker for 15±1 minutes. The slurry is filtered through a dry filter crucible into a dry suction flask.

Measurement: An analysis sample is made in the same manner as the calibration solutions but using 5.0 ml of filtrate instead of standard solution, and the measurement is carried out as described above.

Results

Calculation: The content of $Cr^{+6}$ in the solution is read off from the calibration curve. The content of water-soluble chromate in the cement is calculated from the formula x = y/5 in which x = the content of water-soluble chromate in the cement expressed as mg of $Cr^{+6}$ per kg of cement.

y = the content of $Cr^{+6}$ (μg) in the solution, read off from the calibration curve.

For the final result, the mean of two determinations not varying more than 0.4 mg/kg from one another is used.

In this example, manganese(II) sulfate was interground with chromate-containing cement clinker and gypsum to investigate the ability of manganese(II) sulfate to reduce water soluble chromate in cement.

The following materials were used:

Manganese(II) sulfate of technical grade of Chinese origin. It contained more than 31% manganese and it was obtained from Superfos Kemikalier A/S, Denmark. $MnSO_4.H_2O$ and $MnSO_4$ was detected by examination with X-ray diffraction.

Gypsum of technical grade from Boliden, Sweden.

Cement clinker manufactured by Norcem A.S., Norway. The chemical composition of the clinker was:

| | |
|---|---|
| $SiO_2$ | 20.61% |
| $Al_2O_3$ | 4.99% |
| $Fe_2O_3$ | 3.55% |
| CaO | 64.81% |
| MgO | 2.46% |
| $SO_3$ | 1.68% |
| $K_2O$ | 1.30% |
| $Na_2O$ | 0.38% |

Water soluble chromate: 28.3 mg of $Cr^{+6}$/kg (Determined by elution with 20% sodium sulfate solution for 15 minutes at a water to clinker ratio of 1)

Cement clinker, 5% gypsum and varying amounts of manganese(II) sulfate was interground in a laboratory mill to a specific surface according to Blaine of 410–510 $m^2$/kg. Propylene glycol was added as a grinding agent in a dosage of 0.05%.

The content of water-soluble chromate was determined according to Dansk Standard DS 1020 (First Edition, July, 1984).

Measurements of the reduction capacity of the cement mixes were also carried out.

These measuring methods were also used in examples 2–5.

The results of the measurements are given in Table 1 below.

TABLE 1

| Reducing agent | Dosage (%) | Water soluble chromate (mg $Cr^{+6}$/kg cement) | Chromate in filtrate | | Reduction capacity | Blaine surface of the cement ($m^2$/kg) |
|---|---|---|---|---|---|---|
| Chromate in added water | | 0.0 | 50 | 100 | | |
| (Plain cement) | 0.00 | 19.7* | 67 | 112 | −23 | 506 |
| Manganese (II) | 0.25 | 2.9 | 32 | 73 | 11 | 500 |
| sulfate, | 0.30 | 0.2 | 25 | 62 | 16 | 454 |
| technical grade | 0.40 | 0.1 | 18 | 50 | 21 | 437 |
| | 0.50 | 0.0 | 1 | 17 | 48 | 492 |
| | 0.75 | 0.0 | 0 | 0 | >50 | 500 |
| $MnSO_4.H_2O$, | 0.25 | 7.4 | 40 | 80 | 1 | 417 |
| analytical grade | 0.50 | 0.0 | 0 | 1 | >50 | 498 |

*The content of water soluble chromate in the plain cement was 25.0 mg $Cr^{+6}$/kg when the determination was carried out by elution with 20% sodium sulfate solution.

The results show that manganese(II) sulfate when interground with cement is an efficient chromate reducing agent and that a low dosage of manganese(II) sulfate is sufficient to reduce all water-soluble chromate.

EXAMPLE 2

Manganese(II) sulfate was mixed with chromate containing cement to investigate the ability of unground manganese(II) sulfate to reduce soluble chromate in cement.

The manganese(II) sulfate of technical grade and the plain cement from example 1 were used. The manganese(II) sulfate was a free flowing white powder with a 0.045 mm sieve residue of 48%.

The cement mixes were prepared by mixing plain cement and manganese(II) sulfate in a plastic bucket with a paint mixer for 3 minutes.

The content of water-soluble chromate and the reduction capacity was measured.

The results of the measurements are given in Table 2 below.

TABLE 2

| Reducing agent | Dosage (%) | Water soluble chromate (mg $Cr^{+6}$/kg cement) | Chromate in filtrate | | Reduction capacity |
|---|---|---|---|---|---|
| Chromate in added water | | 0.0 | 50 | 100 | |
| (Plain cement) | 0.00 | 19.7 | 67 | 112 | −23 |
| Manganese (II) | 0.25 | 13.4 | 53 | 96 | −13 |
| sulfate, | 0.50 | 7.0 | 39 | 76 | −3 |
| technical grade | 1.00 | 0.7 | 19 | 45 | 16 |
| | 1.50 | 0.0 | 3 | 20 | 43 |
| | 2.00 | 0.0 | 0 | 5 | >50 |
| | 2.50 | 0.0 | 0 | 2 | >50 |

The results show that unground manganese(II) sulfate is able to reduce water soluble chromate in cement. When the results of examples 1 and 2 are compared it can be seen that a lower dosage of manganese(II) sulfate is needed to reduce the water soluble chromate to less than 2 mg of $Cr^{+6}$/kg when the manganese(II) sulfate is interground with cement than when it is only mixed with the cement.

EXAMPLE 3

Manganese(II) sulfate, manganese(II) carbonate and iron(II) sulfate were interground with chromate-containing cement clinker and gypsum to investigate the ability of these compounds to reduce water soluble chromate in cement.

The following materials were used:

Manganese(II) sulfate of technical grade from example 1.

Manganese(II) carbonate hydrate, $MnCO_3.xH_2O$, of analytical grade.

Iron(II) sulfate monohydrate, $FeSO_4.H_2O$ prepared by drying of analytical grade $FeSO_4.7H_2O$ in a nitrogen atmosphere at 120° C.

Iron(II)sulfate heptahydrate, $FeSO_4.7H_2O$, of analytical grade.

Cement clinker from Aalborg Portland produced in kiln 87 on Nov. 21, 1990. The content of water soluble chromate was 6,2 mg of $Cr^{+6}$/kg. (Determined by elution with 20% sodium sulfate solution for 15 minutes at a water to clinker ratio of 1).

Gypsum of technical grade from Boliden, Sweden.

Cement clinker, 5% gypsum and varying amounts of chromate reducing agent were interground in a laboratory mill to a specific surface of 390–530 $m^2$/kg. Propylene glycol was added as a grinding agent in a dosage of 0.05%.

The content of water soluble chromate and the reduction capacity was measured.

The results of the measurements are given in Table 3 below.

ground with cement. Manganese(II) carbonate was also able to reduce chromate when interground with cement.

EXAMPLE 4

The cements from example 3 containing manganese(II) sulfate and iron(II) sulfate were heated to temperatures of 100°, 150°, 200°, 250° and 400° C. to determine the ability of the cements to withstand elevated temperatures.

Heat treatment of the cements were carried out by placing 100 g of the cement in aluminium trays without lid and placing the aluminium trays for 3 hours at the desired temperatures.

Cement which was heat-treated at 400° C. was mixed with 4% calcium sulfate hemihydrate before elution for determination of water soluble chromate and reduction capacity.

The content of water soluble chromate in the cements and the reduction capacity was measured.

TABLE 3

| Reducing agent | Dosage (%) | Water soluble chromate | Chromate in filtrate (mg $Cr^{+6}$/kg cement) | | Reduction capacity | Blaine surface of the cement ($m^2$/kg) |
|---|---|---|---|---|---|---|
| Chromate in added water | | 0.0 | 50 | 100 | | |
| (Plain cement) | 0.00 | 3.2* | 44 | 85 | −5 | 486 |
| Manganese (II) | 0.25 | 0.0 | 16 | 48 | 25 | 460 |
| sulfate, | 0.50 | 0.0 | 1 | 15 | 48 | 403 |
| technical grade | | | | | | |
| $MnCO_3.H_2O$, | 0.25 | 1.7 | 42 | 82 | −3 | 498 |
| analytical grade | 0.50 | 0.0 | 32 | 71 | 9 | 496 |
| | 1.00 | 0.0 | 33 | 73 | 9 | 430 |
| | 2.00 | 0.0 | 0 | 0 | 50 | 530 |
| $FeSO_4.H_2O$ | 0.25 | 0.0 | 20 | 61 | 25 | 395 |
| | 0.50 | 0.0 | 0 | 34 | 50 | 406 |
| $FeSO_4.7H_2O$, | 0.25 | 0.0 | 0 | 25 | >50 | 429 |
| analytical grade | 0.50 | 0.0 | 0 | 0 | >50 | 493 |

*The content of water soluble chromate in the plain cement was 5.1 mg of $Cr^{+6}$/kg when the determination was carried out by elution with 20% sodium sulfate solution.

The results show that manganese(II) sulfate is an efficient chromate reducing agent when it is inter- The results of the measurements are given in Table 4 below.

TABLE 4

| Cements heated to 100, 150, 200, 250 and 400° C. for 3 hours | | | | | | |
|---|---|---|---|---|---|---|
| Reducing agent | Dosage (%) | Temperature of heat treatment (°C.) | Water soluble chromate | Chromate in filtrate (mg $Cr^{+6}$/kg cement) | | Reduction capacity |
| Chromate in added water | | | 0.0 | 50 | 100 | |
| (Plain cement) | 0.00 | 100 | 3.4 | 48 | 88 | −4 |
| | | 150 | 3.6 | | | |
| | | 200 | 3.8 | | | |
| | | 250 | 3.9 | | | |
| | | 400 | 4.5 | | | |
| Manganese (II) | 0.25 | 100 | 0.0 | 13 | 43 | 29 |
| sulfate, | 0.25 | 150 | 0.0 | 6 | 40 | 40 |
| technical grade | 0.25 | 200 | 0.0 | 13 | 44 | 29 |
| | 0.25 | 250 | 0.0 | 18 | 48 | 18 |
| | 0.25 | 400 | 0.0 | 22 | 71 | 27 |
| | 0.50 | 100 | 0.0 | 0 | 7 | >50 |
| | 0.50 | 150 | 0.0 | 0 | 6 | >50 |
| | 0.50 | 200 | 0.0 | 0 | 8 | >50 |
| | 0.50 | 250 | 0.0 | 0 | 0 | >50 |
| | 0.50 | 400 | 0.0 | 15 | 46 | 25 |
| $FeSO_4.H_2O$ | 0.25 | 100 | 0.0 | 19 | 59 | 27 |
| | 0.25 | 150 | 0.0 | 18 | 60 | 28 |
| | 0.25 | 200 | 0.0 | 29 | 71 | 15 |
| | 0.25 | 250 | 0.0 | 40 | 80 | 1 |
| | 0.25 | 400 | 0.2 | 40 | 83 | 2 |
| | 0.50 | 100 | 0.0 | 0 | 25 | >50 |
| | 0.50 | 150 | 0.0 | 0 | 26 | >50 |

TABLE 4-continued

Cements heated to 100, 150, 200, 250 and 400° C. for 3 hours

| Reducing agent | Dosage (%) | Temperature of heat treatment (°C.) | Water soluble chromate | Chromate in filtrate (mg Cr$^{+6}$/kg cement) | | Reduction capacity |
|---|---|---|---|---|---|---|
| | 0.50 | 200 | 0.0 | 13 | 54 | 34 |
| | 0.50 | 250 | 0.0 | 24 | 66 | 22 |
| | 0.50 | 400 | 0.0 | 32 | 73 | 22 |
| FeSO$_4$.H$_2$O, analytical grade | 0.25 | 100 | 0.0 | 7 | 47 | 41 |
| | 0.25 | 150 | 0.0 | 23 | 62 | 22 |
| | 0.25 | 200 | 0.0 | 30 | 70 | 13 |
| | 0.25 | 250 | 0.0 | 41 | 84 | −2 |
| | 0.25 | 400 | 4.5 | | | |
| | 0.50 | 100 | 0.0 | 0 | 7 | >50 |
| | 0.50 | 150 | 0.0 | 15 | 52 | 30 |
| | 0.50 | 200 | 0.0 | 19 | 60 | 27 |
| | 0.50 | 250 | 0.0 | 28 | 69 | 15 |
| | 0.50 | 400 | 3.2 | | | |

In industrial cement milling systems, the temperature is normally elevated due to release of heat from the grinding process and due to residual heat in the clinker.

The results show that manganese(II) sulfate has a better ability to withstand elevated temperatures than iron(II) sulfate. When the chromate reducing agent is added during cement grinding the dosage which is necessary to reduce water soluble chromate may be lower for manganese(II) sulfate than for iron(II) sulfate.

EXAMPLE 5

Manganese(II) chloride, manganese(II) acetate, manganese(II) nitrate and manganese(II) sulfate were mixed with chromate-containing cement to determine the ability of these manganese(II) salts to reduce water soluble chromate in cement. Furthermore, manganese(II) sulfate was added in dissolved form to the cement.

The following materials were used:
Manganese(II) chloride, MnCl$_2$.4H$_2$O, of analytical grade
Manganese(II) acetate, Mn(C$_2$H$_5$O$_2$)$_2$.4H$_2$O, of analytical grade
Manganese(II) nitrate, Mn(NO$_3$)$_2$.4H$_2$O, of analytical grade
Manganese(II) sulfate, MnSO$_4$.H$_2$O, of analytical grade
Manganese(II) sulfate of technical grade from example 1.
Ordinary Portland cement of Polish origin with a water soluble chromate content of 9.4 mg of Cr$^{+6}$/kg.

Mixes of the cement and the manganese(II) salts were prepared by mixing cement and unground manganese(II) salts in a paint mixer for 1 minute.

The content of water soluble chromate was determined according to Dansk Standard DS 1020 the same day as the mixes were prepared and again after standing for 14 days.

The following procedure was used when manganese(II) sulfate was added to the cement in dissolved form. Solutions containing 0.05%, 0.10% and 0.25% MnSO$_4$.H$_2$O of analytical grade were made and immediately used for elution of the cement. Determination of chromate were carried out according to Dansk Standard DS 1020 except that the manganese(II) sulfate solutions were used for elution instead of pure water.

The results of the measurements are given in Table 5 and 6 below.

TABLE 5

Water soluble chromate (mg Cr$^{+6}$/kg) in cement mixes

| Dosage (%) | MnCl$_2$.4H$_2$O | Mn(C$_2$H$_5$O$_2$)$_2$.4H$_2$O (mg Cr$^{+6}$/kg) | Mn(NO$_3$)$_2$.4H$_2$O |
|---|---|---|---|
| 0.10 | 1.3 | 3.7 | 9.1 |
| 0.25 | 0.0 | 0.0 | 2.7 |
| 0.50 | 0.0 | 0.0 | 0.9 |
| 0.75 | | | 0.0 |

| Dosage (%) | MnSO$_4$.H$_2$O | Manganese (II) sulfate, technical grade (mg Cr$^{+6}$/kg) | MnSO$_4$.H$_2$O dissolved in mixing water |
|---|---|---|---|
| 0.05 | | | 6.4 |
| 0.10 | 10.0 | 9.3 | 0.3 |
| 0.25 | 7.9 | 7.4 | 0.0 |
| 0.50 | 4.6 | 3.9 | |
| 0.75 | 1.2 | 2.0 | |
| 1.00 | 0.3 | 0.5 | |
| 1.50 | 0.1 | 0.1 | |
| 2.00 | 0.0 | 0.0 | |

TABLE 6

Water soluble chromate (mg Cr$^{+6}$/kg) after 14 days

| Dosage (%) | MnCl$_2$.4H$_2$O | Mn(C$_2$H$_5$O$_2$)$_2$.4H$_2$O (mg Cr$^{+6}$/kg) | Mn(NO$_3$)$_2$.4H$_2$O |
|---|---|---|---|
| 0.10 | 2.6 | 4.2 | 9.0 |
| 0.25 | 0.0 | 0.0 | 7.0 |
| 0.50 | 0.0 | 0.0 | 5.3 |
| 0.75 | | | 2.4 |

| Dosage (%) | MnSO$_4$.H$_2$O | Manganese (II) sulfate, technical grade (mg Cr$^{+6}$/kg) |
|---|---|---|
| 0.10 | 9.4 | 9.4 |
| 0.25 | 6.7 | 7.2 |
| 0.50 | 3.5 | 4.1 |
| 0.75 | 1.9 | 2.1 |
| 1.00 | 0.5 | 0.1 |
| 1.50 | 0.1 | 0.0 |
| 2.00 | 0.0 | 0.0 |

The results show that manganese(II) chloride, manganese(II) acetate, manganese(II) nitrate and dissolved manganese(II) sulfate are able to reduce water soluble chromate in cement.

The results also show that manganese(II) chloride tetrahydrate and manganese(II) acetate tetrahydrate are more efficient chromate reducing agents than manganese(II) sulfate monohydrate.

The results further show that manganese(II) chloride, manganese(II) acetate and manganese(II) sulfate are stable towards oxidation by air in dry cement mixes. Manganese(II) nitrate is stable towards oxidation in pure form but when mixed with cement the results indicate that manganese(II) nitrate is partly oxidized by standing with time.

I claim:

1. A cement composition comprising:
   1) a cement containing water-soluble chromate; and
   2) at least one manganese(II) compound in an amount sufficient to reduce the amount of water-soluble chromate to at most 2 mg of Cr(VI) per kg of the cement, wherein the chromate content is determined by (a) elution of the composition in water for 15 minutes at a water to cement ratio of 1, (b) filtration, and (c) determining the chromate content in the filtrate, and wherein the manganese(II) compound is selected from the group consisting of (i) a salt with a mineral acid selected from the group consisting of sulfates, hydrogen sulfates, carbonates, nitrates, nitrites, sulfites, sulfides, disulfides, dithionates, thiosulfates, thiocyanates, hydroxides, oxides, monohydrogen phosphates, dihydrogen phosphates and silicates, or hydrates thereof; (ii) a double salt with a mineral acid; (iii) a salt with an organic acid selected from the group consisting of alkanoic acids, hydroxycarboxylic acids and sulfonic acids: and (iv) manganese(II) oxide sulfate.

2. A composition as claimed in claim 1, wherein the manganese(II) compound is present in an amount sufficient to reduce the amount of water-soluble chromate to at most 0.5 mg of Cr(VI) per kg of the cement.

3. A composition as claimed in claim 2, wherein the manganese(II) compound Is present in an amount sufficient to reduce the amount of water-soluble chromate to at most 0.1 mg of Cr(VI) per kg of the cement.

4. A composition as claimed in claim 3, wherein the manganese(II) compound is present in an amount sufficient to reduce the amount of water-soluble chromate to at most 0.01 mg of Cr(VI) per kg of the cement.

5. A composition as claimed in claim 1, wherein the manganese(II) compound is present in an amount within the range of from 1 to 1000 mmol manganese(II) per kg of cement.

6. A composition as claimed in claim 5, wherein the manganese(II) compound is present in an amount within the range of from 5 to 100 mmol manganese(II) per kg of cement.

7. A composition as claimed in claim 6, wherein the manganese(II) compound is present in an amount within the range of from 10 to 60 mmol manganese(II) per kg of cement.

8. A composition as claimed in claim 1, wherein the manganese ( II ) compound is a salt with a mineral acid or with an organic acid.

9. A composition as claimed in claim 8, wherein the mineral acid salt is selected from the group consisting of sulfate, carbonate, and nitrate.

10. A composition as claimed in claim 9, wherein the mineral acid salt is the sulfate.

11. A composition as claimed in claim 10, wherein the manganese(II) sulfate is present in an amount within the range of 0.01 to 10% by weight based on the weight of the cement.

12. A composition as claimed in claim 11, wherein the manganese(II) sulfate is present in an amount within the range of 0.1 to 1% by weight based on the weight of the cement.

13. A composition as claimed in claim 8, wherein the organic acid salt is a salt with an acid selected from the group consisting of sulfonic acid, alkanoic acid and acetic acid.

14. A composition as claimed in claim 1, wherein the cement is selected from the group consisting of Portland cement, belite cement, and slag cement.

15. A composition as claimed in claim 14, wherein the cement is a Portland cement.

16. A composition as claimed in claim 1, wherein the composition further comprises at least one material selected from the group consisting of aggregate material, reinforcing material and slaked lime.

17. A composition as claimed in claim 16, wherein the aggregate material is selected from the group consisting of fine aggregate and coarse aggregate.

18. A composition as claimed in claim 1, wherein the composition is in the dry form and the manganese(II) compound is in the form of particles having a mean particle size below 0.1 mm.

19. A composition as claimed in claim 18, wherein the composition is in the dry form and the manganese(II) compound is in the form of particles having a mean particle size below 0.05 mm.

20. A composition as claimed in claim 19, wherein the composition is in the dry form and the manganese(II) compound is in the form of particles having a mean particle size below 0.02 mm.

21. A method for reducing the amount of water-soluble chromate in a cement composition, said method comprising adding to a cement composition comprising a water-soluble chromate, a manganese(II) compound in an amount sufficient to reduce the amount of water-soluble chromate to at most 2 mg of Cr(VI) per kg of cement, and wherein the manganese(II) compound is selected from the group consisting of (i) a salt with a mineral acid selected from the group consisting of sulfates, hydrogen sulfates, carbonates, nitrates, nitrites, sulfites, sulfides, disulfides, dithionates, thiosulfates, thiocyanates, hydroxides, oxides, monohydrogen phosphates, dihydrogen phosphates and silicates, or hydrates thereof; (ii) a double salt with a mineral acid; (ii) a salt with an organic acid selected from the group consisting of alkanoic acids, hydroxycarboxylic acids and sulfonic acids; and (iv) manganese(II) oxide sulfate.

22. A method as claimed in claim 21, wherein the manganese(II) compound is added according to at least one of the methods selected from the group consisting of:
   (i) addition to cement clinker prior to or during grinding;
   (ii) addition to semi-ground cement clinker;
   (iii) addition to a component added during the production of cement;
   (iv) addition as a concentrated aqueous solution to clinker in such a manner that the solution is evaporated by adding the solution to the clinker while the clinker are still warm, or where the clinker are heated mechanically;
   (v) addition to cement powder prior to or during transfer thereof to storage or transport;
   (vi) addition to cement powder prior to or during packaging thereof;
   (vii) addition to cement powder during transfer thereof from a transport vehicle to storage;
   (viii) addition to cement powder or a composition containing cement powder prior to mixing thereof with water; and (ix) addition as a solution in cement mixing water.

23. A method as claimed in claim 21, wherein manganese(II) sulfate is added to a cement composition in an amount within the range of 0.01 to 10% by weight based on the weight of the cement.

24. A method as claimed in claim 23, wherein manganese(II) sulfate is added to a cement composition in an amount within the range of 0.1 to 1% by weight based on the weight of the cement.

25. A composition as claimed in claim 1, wherein the cement is a pozzolan cement.

26. A composition as claimed in claim 1, wherein the composition further comprises water.

27. A composition as claimed in claim 1, wherein the composition further comprises cement or concrete additives selected from the group consisting of a retarding agent, a concrete plasticizer, a concrete superplasticizer and an air entraining agent.

28. A cement composition comprising:
1) a cement containing water-soluble chromate; and
2) at least one manganese(II) compound in an amount sufficient to reduce the amount of water-soluble chromate to at most 1mg of Cr(VI) per kg of the cement, wherein the chromate content is determined by (a) elution of the composition in water for 15 minutes at a water to cement ratio of 1, (b) filtration, and (c) determining the chromate content in the filtrate, and wherein the manganese(II) compound selected from the group consisting of (i) a salt with a mineral acid Selected from the group consisting of sulfates, hydrogen sulfates, carbonates, nitrates, nitrites, sulfites, sulfides, disulfides dithionates, thiosulfates, thiocyanates, hydroxides, oxides, monohydrogen, phosphates, dihydrogen phosphates and silicates, or hydrates thereof; (ii) a double salt with a mineral acid; (iii) a salt with an organic acid selected from the group consisting of alkanoic acids, hydroxycarboxylic acids and sulfonic acids; and (iv) manganese(II) oxide sulfate.

29. A composition as claimed in claim 28, wherein the manganese(II) compound is present in an amount within the range of from 1 to 1000 mmol manganese(II) per kg of cement.

30. A composition as claimed in claim 28, wherein the manganese(II) compound is manganese sulfate.

31. A composition as claimed in claim 30, wherein the manganese(II) sulfate is present in an amount within the range of 0.01 to 10% by weight based on the weight of the cement.

32. A composition as claimed in claim 28, wherein the cement is selected from the group consisting of Portland cement, belite cement, and slag cement.

33. A composition as claimed in claim 28, wherein the composition further comprises cement or concrete additives selected from the group consisting of a retarding agent, a concrete plasticizer, a concrete superplasticizer and an air entraining agent.

34. A composition as claimed in claim 28, wherein the composition further comprises a reinforcing material or slaked lime.

35. A composition as claimed in claim 28, wherein the composition is in the dry form and the manganese(II) compound is in the form of particles having a mean particle size below 0.1 mm.

36. A composition as claimed in claim 28, wherein the composition further comprises an aggregate material.

* * * * *